United States Patent
Eom et al.

(10) Patent No.: US 10,238,312 B2
(45) Date of Patent: Mar. 26, 2019

(54) WRIST-TYPE BODY COMPONENT MEASURING APPARATUS AND BODY COMPONENT MEASURING METHOD USING THE SAME

(71) Applicant: SAMSUNG ELECTRONICS CO., LTD., Suwon-si (KR)

(72) Inventors: Kunsun Eom, Seoul (KR); Yeolho Lee, Anyang-si (KR); Kak Namkoong, Seoul (KR); Myounghoon Jung, Bucheon-si (KR); Seongho Cho, Gwacheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 734 days.

(21) Appl. No.: 14/804,718

(22) Filed: Jul. 21, 2015

(65) Prior Publication Data
US 2016/0128604 A1  May 12, 2016

(30) Foreign Application Priority Data
Nov. 7, 2014  (KR) .......................... 10-2014-0154732

(51) Int. Cl.
*A61B 5/053* (2006.01)
*A61B 5/00* (2006.01)
(Continued)

(52) U.S. Cl.
CPC ............ *A61B 5/0537* (2013.01); *A61B 5/065* (2013.01); *A61B 5/067* (2013.01); *A61B 5/068* (2013.01);
(Continued)

(58) Field of Classification Search
CPC ..... A61B 5/0537; A61B 5/681; A61B 5/0533; A61B 5/067; A61B 5/065; A61B 5/068
See application file for complete search history.

(56) References Cited

U.S. PATENT DOCUMENTS 6,132,387 A * 10/2000 Gozani ................ A61B 5/0488
600/554
6,694,182 B1 * 2/2004 Yamazaki .......... A61B 5/02438
600/547
(Continued)

FOREIGN PATENT DOCUMENTS

| JP | 11299752 A | 11/1999 |
|----|-----------|---------|
| JP | 200051173 A | 2/2000 |

(Continued)

*Primary Examiner* — Lee S Cohen
*Assistant Examiner* — Erin M Cardinal
(74) *Attorney, Agent, or Firm* — Sughrue Mion, PLLC

(57) ABSTRACT

Provided is a wrist-type body component measuring apparatus. The wrist-type body component measuring apparatus includes: a band configured to be worn on a wrist of a user; a first input electrode and a first output electrode disposed on an inside surface of the band and configured to be in contact with the wrist of the user; a second input electrode and a second output electrode disposed on an outside surface of the band; a measuring unit configured to apply a current to the first and second input electrodes and detect a voltage from the first and second output electrodes to measure a body impedance of the user; and an electrode converter configured to convert a disposition of the first and second input electrodes and the first and second output electrodes based on a determination of whether the band is worn on a left wrist or a right wrist of the user.

16 Claims, 11 Drawing Sheets

(51) Int. Cl.
*A61B 5/06* (2006.01)
*A61B 5/024* (2006.01)
*A61B 5/0402* (2006.01)
*A61B 5/0205* (2006.01)

(52) U.S. Cl.
CPC ............ *A61B 5/681* (2013.01); *A61B 5/0205* (2013.01); *A61B 5/02416* (2013.01); *A61B 5/0402* (2013.01); *A61B 5/0533* (2013.01)

(56) References Cited

U.S. PATENT DOCUMENTS

| | | | | |
|---|---|---|---|---|
| 6,790,178 B1* | 9/2004 | Mault | .................... | G06F 19/00 600/300 |
| 2004/0059242 A1* | 3/2004 | Masuo | ................. | A61B 5/0537 600/547 |
| 2004/0102931 A1* | 5/2004 | Ellis | ..................... | A61B 5/1038 702/188 |
| 2007/0276270 A1* | 11/2007 | Tran | .................... | A61B 5/0022 600/508 |
| 2008/0281234 A1* | 11/2008 | Goris | .................... | A61B 5/061 600/595 |
| 2010/0076331 A1* | 3/2010 | Chan | ................... | A61B 5/0006 600/522 |
| 2010/0113965 A1* | 5/2010 | Kanevsky | ............ | A61B 5/0531 600/547 |
| 2010/0298656 A1* | 11/2010 | McCombie | ............ | G16H 50/50 600/301 |
| 2013/0137942 A1* | 5/2013 | Karo | .................... | A61B 5/0537 600/301 |
| 2014/0051941 A1* | 2/2014 | Messerschmidt | .... | A61B 5/6898 600/301 |
| 2015/0011854 A1* | 1/2015 | Frix | ....................... | A61B 5/721 600/364 |
| 2016/0051193 A1* | 2/2016 | Park | ....................... | A61B 5/681 600/300 |
| 2016/0054423 A1* | 2/2016 | Kang | ........................ | G06T 7/73 382/203 |
| 2016/0089053 A1* | 3/2016 | Lee | ....................... | A61B 5/0537 600/384 |
| 2016/0198977 A1* | 7/2016 | Eom | ...................... | A61B 5/0537 600/384 |
| 2017/0055869 A1* | 3/2017 | Shin | ................... | A61B 5/04288 |

FOREIGN PATENT DOCUMENTS

| | | |
|---|---|---|
| JP | 2002355230 A | 12/2002 |
| JP | 3899744 B2 | 3/2007 |
| KR | 1020010106959 A | 12/2001 |
| KR | 1020020091489 A | 12/2002 |
| KR | 1020030031246 A | 4/2003 |

\* cited by examiner

WRIST-TYPE BODY COMPONENT MEASURING APPARATUS AND BODY COMPONENT MEASURING METHOD USING THE SAME

CROSS-REFERENCE TO RELATED APPLICATION

This application claims priority from Korean Patent Application No. 10-2014-0154732, filed on Nov. 7, 2014 in the Korean Intellectual Property Office, the disclosure of which is incorporated herein in its entirety by reference.

BACKGROUND

1. Field

Apparatuses and methods consistent with exemplary embodiments relate to body component measuring apparatuses and methods.

2. Description of the Related Art

Interest in healthcare has increased with the development of medical science and the recent extension of the average life span of human beings. In this regard, interest in medical instruments has also increased. The range of this interest has extended not only to various medical instruments used in test organizations, but also to small and medium-sized medical instruments equipped in public institutions, small-sized medical instruments possessed or carried by individual persons, and healthcare apparatuses.

A body component measuring apparatus is a kind of healthcare apparatus. The body component measuring apparatus measures a body component by using a bioelectrical impedance analysis (BIA) method that analyzes a body component by accurately measuring a body impedance depending on the quantity of a body component such as water, protein, bone, or fat included in a human body. The BIA method regards a human body as a combination of impedances, flows a current through the human body, measures a voltage caused by the current, and measures an impedance of the human body from the current and the voltage.

SUMMARY

One or more exemplary embodiments provide body component measuring apparatuses and methods.

According to an aspect of an exemplary embodiment, there is provided a wrist-type body component measuring apparatus including: a band configured to be worn by a user; a first input electrode and a first output electrode disposed on an inside surface of the band and configured to be in contact with a wrist of a user; a second input electrode and a second output electrode disposed on an outside surface of the band; a measuring unit configured to apply a current to the first and second input electrodes and detect a voltage from the first and second output electrodes to measure a body impedance of the user; and an electrode converter configured to convert a disposition of the first and second input electrodes and the first and second output electrodes based on a whether the band is worn on a left wrist or a right wrist of the user.

The measuring unit may include: a current provider configured to apply the current to the first and second input electrodes; a voltage detector configured to detect the voltage from the first and second output electrodes; and an impedance calculator configured to calculate the body impedance from the current and the voltage.

The electrode converter may include a plurality of switches configured to convert terminals of the first and second output electrodes and the first and second input electrodes connected to both terminals of the voltage detector and the current provider.

An arrangement direction of the first input electrode and the first output electrode and an arrangement direction of the second input electrode and the second output electrode may be different from a lengthwise direction of the band.

The arrangement direction of the first input electrode and the first output electrode and the arrangement direction of the second input electrode and the second output electrode may be perpendicular to the lengthwise direction of the band.

The wrist-type body component measuring apparatus may further include a sensor configured to determine whether the band is worn on the left wrist or the right wrist. The electrode disposition is converted such that the first input electrode and the second input electrode are disposed on a hand side and the first output electrode and the second output electrode are disposed on a body side based on the determination.

The wrist-type body component measuring apparatus may further include a sensor disposed to face a radial artery of the user and configured to sense whether the band is worn on the left wrist or on the right wrist by using a biometric signal received from the radial artery.

The sensor may include a light sensor configured to detect an electrocardiography (ECG) signal, a galvanic skin reflex (GSR) signal, a photoplethysmography (PPG) signal, or a pulse wave.

The wrist-type body component measuring apparatus may further include a plurality of sensors arranged in a direction perpendicular to a lengthwise direction of the band with a predetermined distance therebetween, and configured to sense whether the band is worn on the left wrist or on the right wrist by using a signal received according to a movement of the user.

The sensors may include acceleration sensors.

The wrist-type body component measuring apparatus may further include an input unit configured to input information about whether the band is worn on the left wrist or on the right wrist.

A body component of the user may be analyzed from the body impedance measured by the measuring unit, and the body component may include at least one of body fat, body water, skeletal muscle mass, protein, mineral, visceral fat, body cell mass, bone mineral content, muscle strength, and edema.

The wrist-type body component measuring apparatus may include a memory configured to store an impedance of an end body part of the user that is to be in contact with the second input electrode and the second output electrode, for body impedance measurement.

According to an aspect of another exemplary embodiment, there is provided a wrist-type body component measuring apparatus including: a band configured to be worn on a wrist of a user; a first input electrode and a first output electrode disposed on an inside surface of the apparatus to be in contact with the wrist of the user; a second input electrode and a second output electrode disposed on an outside surface of the apparatus; a measuring unit configured to apply a current to the first and second input electrodes and detect a voltage from the first and second output electrodes to measure a body impedance of the user; a memory configured to store a first measurement value in response to the band being worn on a left wrist or a right wrist of the user; and an electrode converter configured to compare the first measurement value stored in the memory and a second measurement value measured by the measurement unit and convert a disposition of the first and second input electrodes and the first and second output electrodes according to whether the apparatus is worn on the left wrist or the right wrist.

The measuring unit may include: a current provider configured to apply the current to the first and second input electrodes; a voltage detector configured to detect the voltage from the first and second output electrodes; and an impedance calculator configured to calculate the impedance of the user from the current and the voltage.

The electrode converter may include a plurality of switches configured to convert terminals of the first and second output electrodes and the first and second input electrodes connected to both terminals of the voltage detector and the current provider.

An arrangement direction of the first input electrode and the first output electrode and an arrangement direction of the second input electrode and the second output electrode may be different from a lengthwise direction of the band.

The arrangement direction of the first input electrode and the first output electrode and the arrangement direction of the second input electrode and the second output electrode may be perpendicular to the lengthwise direction of the band.

According to whether the apparatus is worn on the left wrist or on the right wrist, the electrode disposition may be converted such that the first input electrode and the second input electrode are disposed on a hand side and the first output electrode and the second output electrode are disposed on a body side.

A body component of the user may be analyzed from the body impedance measured by the measuring unit, and the body component may include at least one of body fat, body water, muscle strength, and edema.

The memory may store an impedance of an end body part of the user that is to be in contact with the second input electrode and the second output electrode, for body impedance measurement.

According to an aspect of another exemplary embodiment, there is provide a method of measuring a body component of a user by a wrist-type body component measuring apparatus including first and second input electrodes and first and second output electrodes. The method may include: determining whether the first and second input electrodes are disposed farther from the center of the body of the user than the first and second output electrodes; providing a current between the first input electrode and the second input electrode; measuring a voltage between the first output electrode and the second output electrode; and determining a body impedance of the user based on the measured voltage.

The body component measuring method may further include converting an electrode disposition of the first and second input electrodes and the first and second output electrodes in response to the first and second input electrodes being disposed farther from the center of the body than of the first and second output electrodes.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1A:
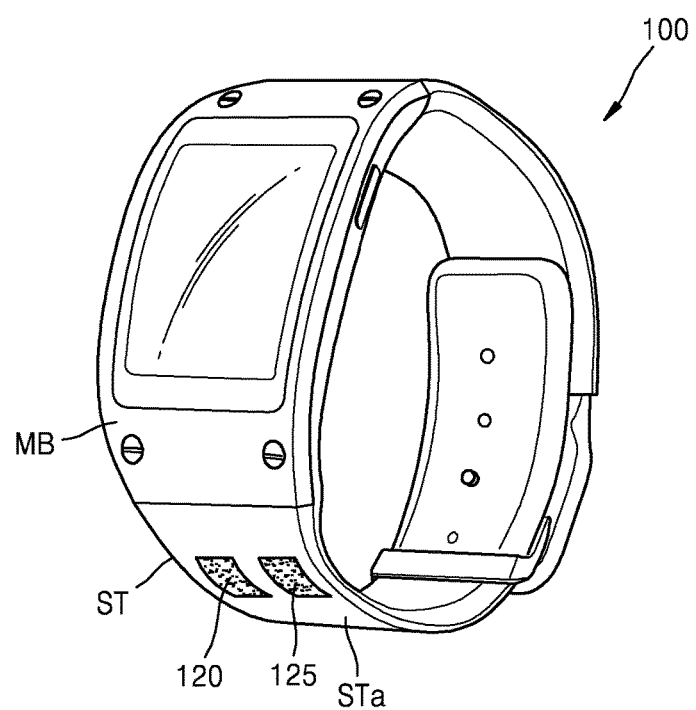
FIGS. 1A and 1B are perspective views of a wrist-type body component measuring apparatus according to an exemplary embodiment, which illustrate an outside surface and an inside surface of a strap respectively.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail. As used herein, expressions such as "at least one of," when preceding a list of elements, modify the entire list of elements and do not modify the individual elements of the list.

It will be understood that when a layer is referred to as being "on" another layer or substrate, it may be directly on the other layer or substrate, or one or more intervening layers may also be present.

Although terms such as "first" and "second" may be used herein to describe various elements or components, these elements or components should not be limited by these terms. These terms are only used to distinguish one element or component from another element or component.

As used herein, the singular forms "a", "an", and "the" are intended to include the plural forms as well, unless the context clearly indicates otherwise. It will also be understood that the terms "comprises", "includes", and "has", when used herein, specify the presence of stated elements, but do not preclude the presence or addition of other elements, unless otherwise defined.

Figure 1B:
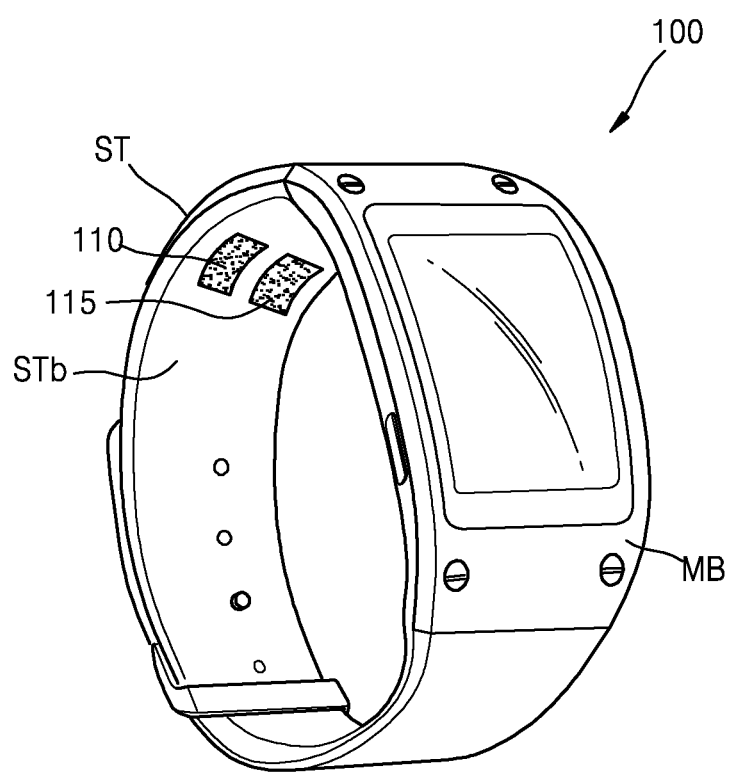
Figure 2:
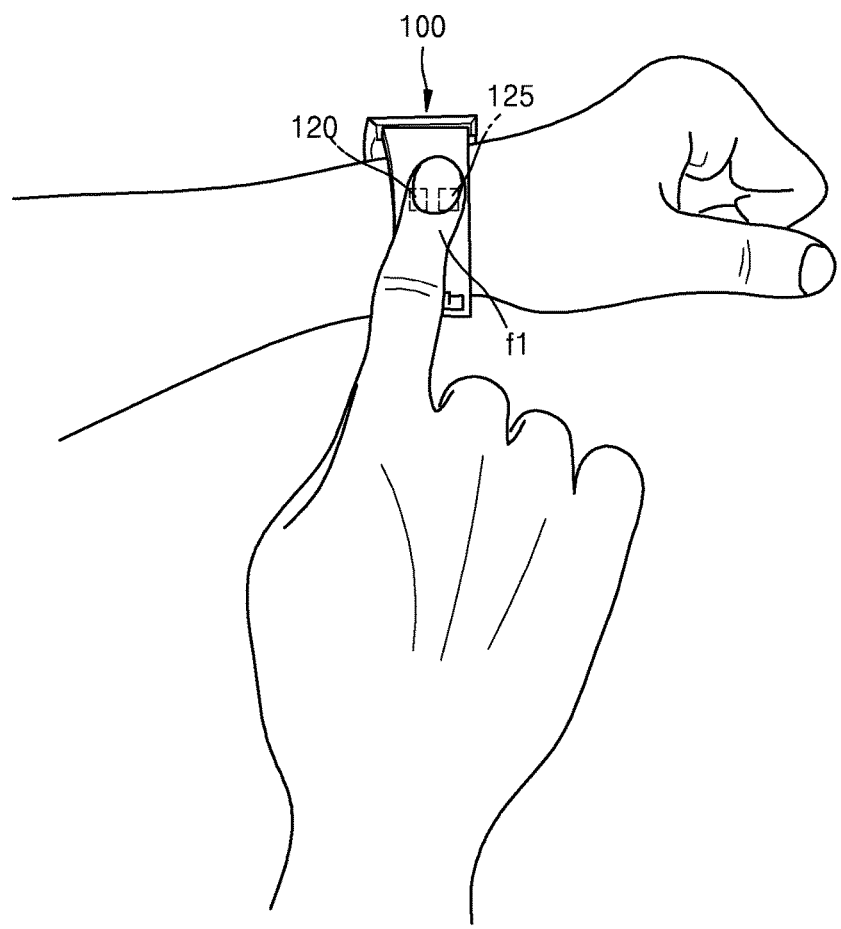
FIG. 2 illustrates an example of a body component measurement posture using the wrist-type body component measuring apparatus according to an exemplary embodiment.

FIGS. 1A and 1B are perspective views of a wrist-type body component measuring apparatus 100 according to an exemplary embodiment, which illustrate an outside surface and an inside surface of a strap respectively. FIG. 2 illustrates an example of a body component measurement posture using the wrist-type body component measuring apparatus 100 according to an exemplary embodiment.

Referring to FIGS. 1A, 1B, and 2, the wrist-type body component measuring apparatus 100 includes a band that is wearable on a wrist of a user and includes a main body MB and a strap ST. Two straps ST are provided on both sides of the main body MB such that they are connected to the main body MB to be worn on a wrist of an object. A first input electrode 110 and a first output electrode 115 are formed on an inside surface STb of one of the two straps ST, and a second input electrode 120 and a second output electrode 125 are formed on an outside surface STa thereof.

The first input electrode 110 and the first output electrode 115 are brought into contact with the wrist of the object when the wrist-type body component measuring apparatus 100 is worn on a user that is the object whose body component is to be measured.

The second input electrode 120 and the second output electrode 125 are brought into contact with an end body part of the other wrist on which the wrist-type body component measuring apparatus 100 is not worn. The end body part of the other wrist, which may contact the second input electrode 120 and the second output electrode 125, is not limited to a specific region. For example, a finger, a plurality of fingers, a palm, the back of the hand, or the side of the hand may contact the second input electrode 120 and the second output electrode 125. For measurement, as illustrated in FIG. 2, a finger may contact the second input electrode 120 and the second output electrode 125 simultaneously, or different fingers may contact the second input electrode 120 and the second output electrode 125, respectively.

FIGS. 1A and 1B illustrate that the first input electrode 110 and the first output electrode 115 are disposed on one side of the strap ST opposite to another side of the strap ST on which the second input electrode 120 and the second output electrode 125 are respectively disposed. However, this is merely exemplary, and the first input electrode 110 and the first output electrode 115 may not be accurately opposite to the second input electrode 120 and the second output electrode 125.

The first input electrode 110 and the first output electrode 115 may be disposed on the inside surface STb of the strap ST or an inside surface of the main body MB to directly contact the object when the object wears the wrist-type body component measuring apparatus 100, and the second input electrode 120 and the second output electrode 125 may be disposed on the outside surface STa of the strap ST or an outside surface of the main body MB. In this case, the first input electrode 110 and the first output electrode 115 disposed on the inside surface STb of the strap ST or the inside surface of the main body MB and the second input electrode 120 and the second output electrode 125 disposed on the outside surface STa of the strap ST or the outside surface of the main body MB may be arranged in a direction non-parallel to a lengthwise direction of the strap ST. For example, as illustrated in FIGS. 1A, 1B, and 2, the first input electrode 110 and the first output electrode 115 may be disposed on the inside surface STb of the strap ST, the second input electrode 120 and the second output electrode 125 may be disposed on the outside surface STa of the strap ST. Further, the first input electrode 110, and the first output electrode 115 may be arranged in a direction perpendicular to the lengthwise direction of the strap ST each other, and the second input electrode 120 and the second output electrode 125 may be arranged in the same direction each other. The first input electrode 110, the first output electrode 115, the second input electrode 120, and the second output electrode 125 may form a closed circuit passing through both arms. The length of the path of the closed circuit may be measured to obtain a body impedance. For example, a body impedance may be measured by detecting the length of a path of a closed circuit including two pairs of electrodes, one of which is disposed farther from the center of the body than the other pair of electrodes. A detailed method of measuring the body impedance by using a plurality of electrodes and a relative disposition relationship of the first input electrode 110, the first output electrode 115, the second input electrode 120, and the second output electrode 125 will be described later with reference to FIGS. 3A, 3B, and 4.

Figure 3A:
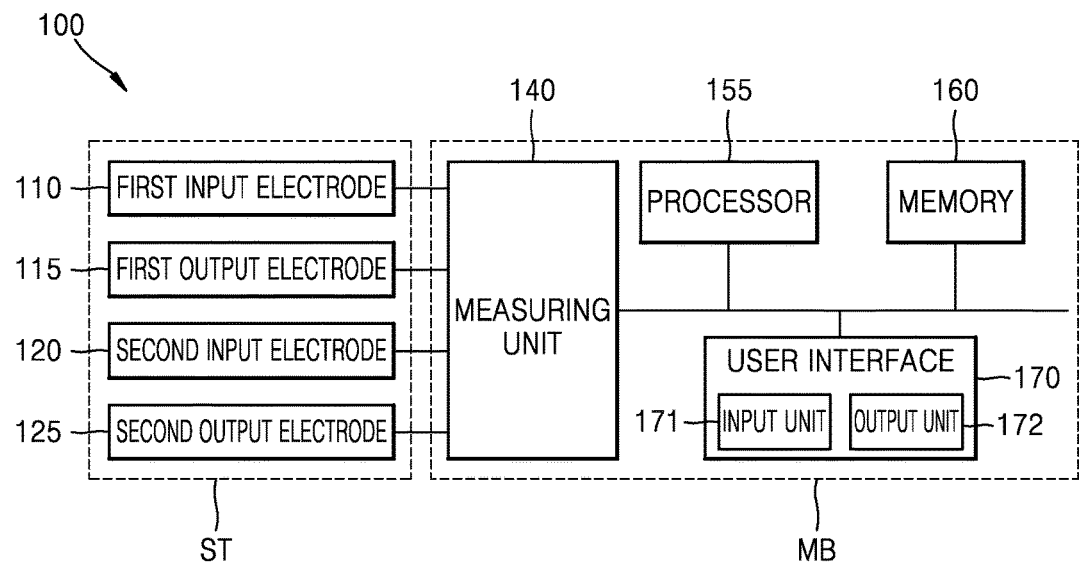
FIG. 3A is a block diagram illustrating a schematic configuration of the wrist-type body component measuring apparatus according to an exemplary embodiment.
Figure 3B:
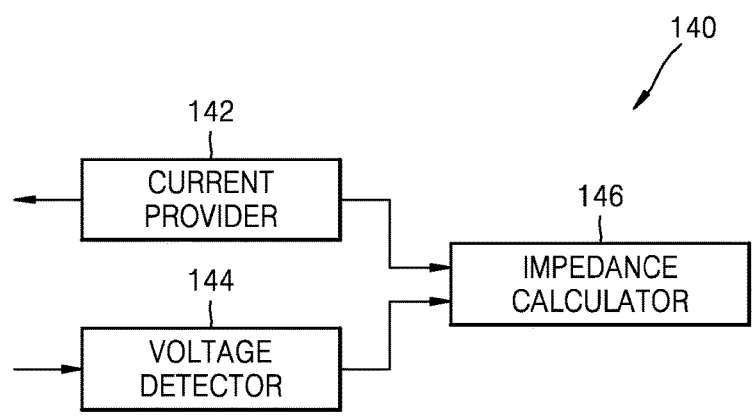
FIG. 3B is a block diagram illustrating an exemplary configuration of a measuring unit included in the wrist-type body component measuring apparatus.
Figure 4A:
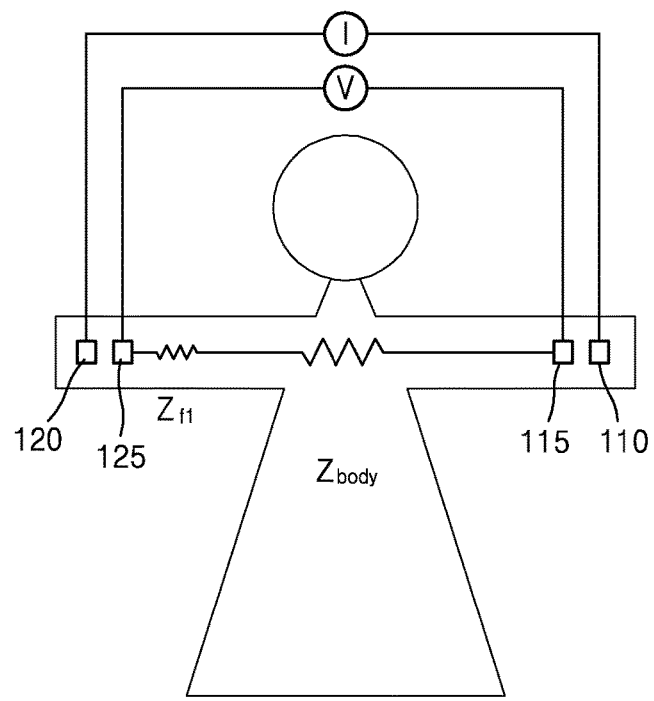
FIG. 4A illustrates a schematic circuit diagram for body impedance measurement in the body component measurement posture illustrated in FIG. 2.
Figure 4B:
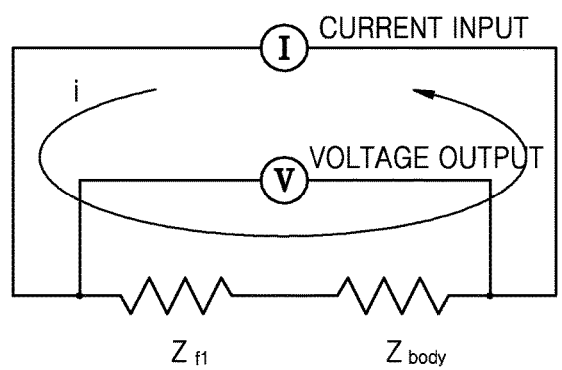
FIG. 4B illustrates an equivalent circuit diagram for body impedance measurement.
Figure 4C:
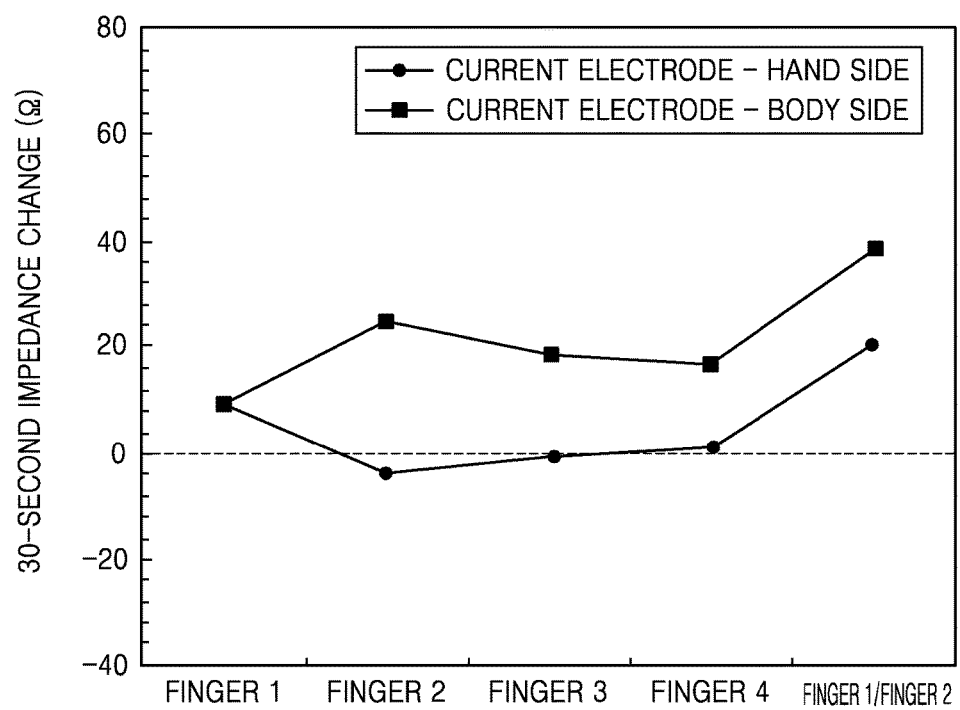
FIG. 4C is a graph illustrating a body impedance change depending on an electrode disposition and an end body part contacting an electrode unit.

FIG. 3A is a block diagram illustrating a schematic configuration of the wrist-type body component measuring apparatus 100 according to an exemplary embodiment. FIG. 3B is a block diagram illustrating an exemplary configuration of a measuring unit 140 included in the wrist-type body component measuring apparatus 100. FIG. 4A illustrates a schematic circuit diagram for body impedance measurement in the body component measurement posture illustrated in FIG. 2. FIG. 4B illustrates an equivalent circuit diagram for body impedance measurement in the body component measurement posture illustrated in FIG. 2. FIG. 4C is a graph illustrating a body impedance change depending on an electrode disposition and an end body part contacting an electrode unit.

Referring to FIGS. 3A and 3B, the measuring unit 140 applies a current to the first input electrode 110 and the second input electrode 120 and detects a voltage from the first output electrode 115 and the second output electrode 125 to measure a body impedance of the object.

The measuring unit 140 may include a current provider 142 configured to apply a current to the first input electrode 110 and the second input electrode 120, a voltage detector 144 configured to detect a voltage between the first output electrode 115 and the second output electrode 125, and an impedance calculator 146 configured to calculate a body impedance of the object by using the applied current and the detected voltage. The voltage detector 144 may include an operational amplifier configured to amplify a voltage between the first output electrode 115 and the second output electrode 125, and a filter configured to remove a noise.

The body impedance measured by the measuring unit 140 may be used by an analyzer to analyze a body component of the object. The analyzer may be stored in the form of a program in a memory 160, and may be executed by a processor 155.

The processor 155 may be hardware that controls the overall function and operation of the wrist-type body component measuring apparatus 100. The processor 155 may analyze the body component by using the body impedance measured by the measuring unit 140 by executing the program stored in the memory 160. Herein, the body component may include body fat, skin characteristics (e.g., body water), muscle strength, or edema of the object.

For example, in addition to analyzing the body component from the body impedance, the processor 155 may control the measuring unit 140 to measure the body impedance and may process image signals to display the body component analysis results.

The processor 155 may be implemented in the form of a microprocessor module or in the form of a combination of two or more microprocessor modules. That is, the processor 155 may be implemented in various forms.

The memory 160 may store a program for operation of the wrist-type body component measuring apparatus 100 and data necessary for this. The memory 160 may include general storage mediums such as a hard disk drive (HDD), a read-only memory (ROM), a random-access memory (RAM), a flash memory, and a memory card.

The memory 160 may store a program for correcting the body impedance measured by the measuring unit 140 and a program for analyzing the body component from the corrected body impedance. Also, the memory 160 may store additional data such as height, weight, and sex. Also, the memory 160 may store an impedance of each end body part of the object, such as, for example, an impedance of a finger, which is necessary for body impedance correction.

A user interface 170 may receive an input for operating the wrist-type body component measuring apparatus 100 from the object, and may output information about the body component of the object processed by the processor 155. The user interface 170 may include an input unit 171 configured to allow the object to operate the wrist-type body component measuring apparatus 100, and an output unit 172 configured to output the results of the wrist-type body component measuring apparatus 100.

The input unit 171 of the user interface 170 may include a button, a keypad, a switch, a dial, or a touch interface that allows the object to operate the wrist-type body component measuring apparatus 100. The output unit 172 of the user interface 170 may include a display configured to display an image, and may be implemented by a touchscreen. The display may include a display panel such as a liquid crystal display (LCD) panel or an organic light-emitting display (OLED) panel, and may display information about the body component analysis results in the form of an image or a text. Also, the user interface 170 may include an input/output (I/O) port for connecting a human interface device (HID), and may include an I/O port for inputting/outputting an image.

The object may input additional data, such as the wear position of the wrist-type body component measuring apparatus 100 and the height, weight, and sex of the object, through the input unit 171 of the user interface 170, and may obtain information about the body component measurement results through the output unit 172 of the user interface 170.

Although FIGS. 1A, 1B, and 3A illustrate that the first input electrode 110, the second input electrode 120, the first output electrode 115, and the second output electrode 125 are disposed in the strap ST and the measuring unit 140, the processor 155, the memory 160, and the user interface 170 are disposed in the main body MB, exemplary embodiments are not limited thereto. The first input electrode 110, the second input electrode 120, the first output electrode 115, and the second output electrode 125 may also be disposed in a divided manner on a front surface and a rear surface of the main body MB to contact the wrist of the object and the end body part of the other wrist on which the wrist-type body component measuring apparatus 100 is not worn. Also, in the wrist-type body component measuring apparatus 100, the first input electrode 110, the second input electrode 120, the first output electrode 115, the second output electrode 125, the measuring unit 140, the processor 155, the memory 160, and the user interface 170 may be modularized and disposed in the main body MB or the strap ST.

Referring to FIGS. 2, 4A, and 4B, the wrist-type body component measuring apparatus 100 may be worn on the left wrist of the object, and a right-hand index finger f1 may be brought into contact with the second input electrode 120 and the second output electrode 125.

In the equivalent impedance of the object, the impedances of the right arm, the body, and the left arm may form a body impedance $Z_{body}$, and the impedance of the right-hand index finger f1 used for measurement is $Z_{f1}$. Since the right-hand index finger f1 contacts the second input electrode 120 and the second output electrode 125 simultaneously, an impedance calculated from a voltage measured through the first output electrode 115 and the second output electrode 125 is $Z_{body}+Z_{f1}$ as illustrated in FIGS. 4A and 4B. The impedance ($Z_{body}+Z_{f1}$) minus the impedance $Z_{f1}$ of the right-hand index finger f1 is the body impedance $Z_{body}$. The impedance $Z_{f1}$ of the right-hand index finger f1 may be pre-measured and stored in the memory 160.

The object may use fingers other than the index finger, such as the big finger, the middle finger, and the ring finger, for measurement. Also in this case, the body impedance may be calculated by correcting the measured impedance from the prestored values such as the big-finger impedance and the middle-finger impedance. As described above, in order to measure the body impedance $Z_{body}$, a pair of input electrodes 110 and 120 and a pair of output electrodes 115 and 125 are disposed in a divided manner on the inside surface STb and the outside surface STa of the wrist-type body component measuring apparatus 100. In an exemplary embodiment, the body impedance $Z_{body}$ is measured by separately calculating and correcting a finger impedance $Z_f$; however, exemplary embodiments are not limited thereto. The total impedance including the finger impedance may be measured. When two or more fingers are brought into contact with electrodes spaced apart from each other with the two or more fingers separated from each other, the body impedance $Z_{body}$ excluding the influence of the finger impedance $Z_f$ may be directly measured.

FIG. 4C is a graph illustrating a body impedance $Z_{body}$ variation in the case where the pair of input electrodes 110 and 120 are disposed on the hand side and in the case where the pair of input electrodes 110 and 120 are disposed on the body side. Referring to FIG. 4C, when the pair of input electrodes 110 and 120 are disposed on the hand side than when the pair of input electrodes 110 and 120 are disposed on the body side, a variation of the body impedance $Z_{body}$, which is measured according to the contact of the end body part (e.g., the index finger, the middle finger, the ring finger, or the index/middle fingers) of the other wrist on which the wrist-type body component measuring apparatus 100 is not worn, is reduced and thus more stable measurement values may be obtained. That is, stable measurement values may be obtained by measuring a voltage on a current path, through which a constant current flows, with a measurement target therebetween. Thus, the pair of input electrodes 110 and 120 may be disposed on the hand side of the object, and the pair of output electrodes 115 and 125 may be disposed on the body side of the object.

As an example, the wrist-type body component measuring apparatus 100 may be worn on the left or right wrist of the object, and the disposition of the pair of input electrodes 110 and 120 and the pair of output electrodes 115 and 125 may be converted according to the wrist on which the wrist-type body component measuring apparatus 100 is worn. For example, referring to FIGS. 1A, 1B, and 2, when the wrist-type body component measuring apparatus 100 is worn on the left wrist, the pair of input electrodes 110 and 120 are disposed on the hand side of the object and the pair of output electrodes 115 and 125 are disposed on the body side of the object. On the other hand, when the wrist-type body component measuring apparatus 100 is worn on the right wrist, the pair of input electrodes 110 and 120 are disposed on the body side of the object and the pair of output electrodes 115 and 125 are disposed on the hand side of the object. Thus, when the wrist on which the wrist-type body component measuring apparatus 100 is worn is determined, a more stable body impedance $Z_{body}$ value may be obtained by adjusting the disposition positions of the plurality of electrodes according to on which wrist, right or left, the wrist-type body component measuring apparatus 100 is worn.

According to an exemplary embodiment, in order to determine the wrist on which the wrist-type body component measuring apparatus 100 is worn, the object may use the input unit 171 of the user interface 170 to input information indicating on which wrist, right or left, the wrist-type body component measuring apparatus 100 is worn.

According to another exemplary embodiment, on which wrist the wrist-type body component measuring apparatus 100 is worn may be determined by using the body impedance $Z_{body}$ value measured by using the plurality of electrodes. Referring to FIGS. 2 and 4C, a variation of the body impedance $Z_{body}$ value in the case where the wrist-type body component measuring apparatus 100 is worn on the left wrist and the pair of input electrodes 110 and 120 and the pair of output electrodes 115 and 125 are disposed on the hand side or the body side may be detected. In this regard, a case where the wrist-type body component measuring apparatus 100 is worn on the left wrist, the pair of input electrodes 110 and 120 are disposed on the hand side, and the pair of output electrodes 115 and 125 are disposed on the body side is set by default, and a first measurement value measured in this case, for example, a variation of a first body impedance $Z_{body}$ is stored in the memory 160. When the wrist-type body component measuring apparatus 100 having the same electrode disposition is worn on the object, a second measurement value, for example, a second body impedance $Z_{body}$ is measured, and a variation equal to a variation of the body impedance $Z_{body}$ value input to the memory 160 is measured, it may be determined that the wrist-type body component measuring apparatus 100 is worn on the left wrist. On the other hand, a variation larger than a measurement value input to the memory 160, for example, a variation of the body impedance $Z_{body}$ is measured, it may be determined that the wrist-type body component measuring apparatus 100 is worn on the right wrist.

According to another exemplary embodiment, in order to determine the wrist on which the wrist-type body component measuring apparatus 100 is worn, a sensor may be used to sense the wrist on which the wrist-type body component measuring apparatus 100 is worn.

Figure 5:
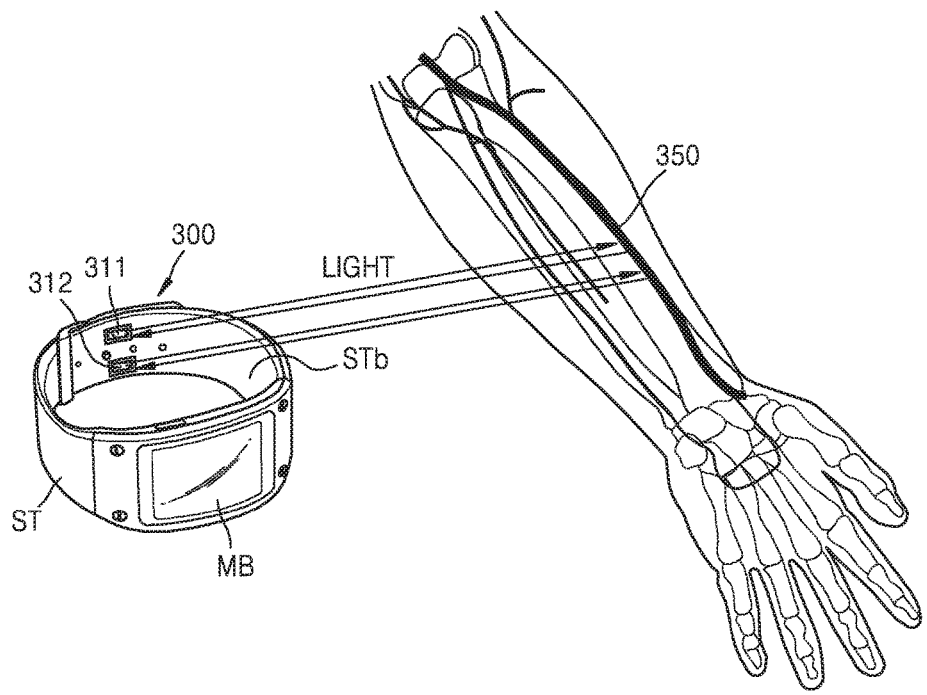
FIG. 5 is a perspective view of a wrist and a biometric signal processing apparatus for detecting biometric signals by using a plurality of sensors according to an exemplary embodiment.
Figure 6:
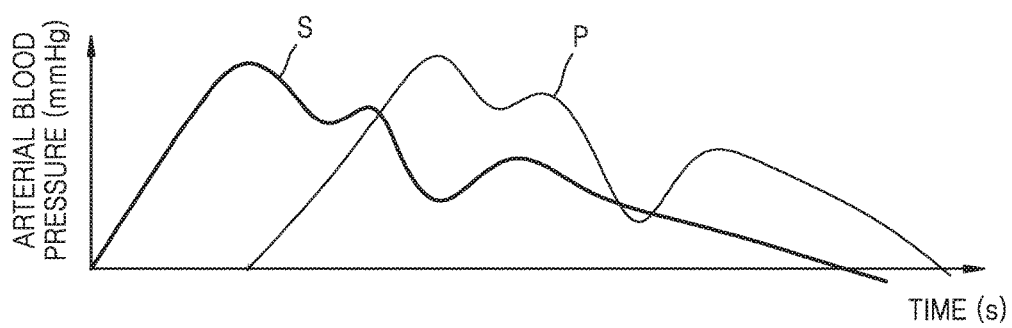
FIG. 6 is a graph illustrating signal waveforms of biometric signals measured by the biometric signal processing apparatus.

FIG. 5 is a perspective view of a wrist and a biometric signal processing apparatus 300 for detecting biometric signals by using a plurality of sensors according to an exemplary embodiment. FIG. 6 is a graph illustrating signal waveforms of biometric signals measured by the biometric signal processing apparatus 300.

Referring to FIG. 5, the biometric signal processing apparatus 300 includes a plurality of light sensors 311 and 312 configured to radiate light in a contact or noncontact manner onto a skin surface above a radial artery 350, and a processor configured to process signals sensed from the light sensors 311 and 312. The light sensors 311 and 312 detect biometric signals of the object, such as an electrocardiography (ECG) signal, a galvanic skin reflex (GSR) signal, a photoplethysmography (PPG) signal, and a pulse wave. The light sensors 311 and 312 may detect biometric signals of the object by using signals reflected by radiating light to the object; however, exemplary embodiments are not limited thereto. Also, the light sensors 311 and 312 may detect biometric signals of the object by using electrical signals, magnetic signals, or pressures.

As an example, in order to measure an arterial blood pressure, the biometric signal processing apparatus 300 may detect a PPG signal by radiating light to the radial artery 350. When a PPG signal is detected from a skin surface of the wrist through which the radial artery 350 passes, the influence of external factors causing a detection error, such as the thickness of a skin tissue in the wrist, may be smallest. Also, it is known that the radial artery 350 is a blood vessel from which a more accurate PPG signal may be detected than from other types of blood vessels in the wrist. However, a blood vessel to which the biometric signal processing apparatus 300 may be applied is not limited to the radial artery 350, and a PPG signal may be detected from blood vessels of other regions of the wrist, other than the radial artery 350. Also, although a method of detecting the biometric signal by photoelectric conversion is described in an exemplary embodiment, exemplary embodiments are not limited thereto and the biometric signal may also be detected by piezoelectric conversion, mechanical conversion, magnetic conversion, or the like.

The first light sensor 311 and the second light sensor 312 may be disposed on the inside surface STb of the strap ST or the main body MB with a predetermined distance therebetween, and may be arranged in a direction perpendicular to the lengthwise direction of the strap ST and disposed to face the radial artery 350. Since the first light sensor 311 and the second light sensor 312 are spaced apart from each other by a predetermined distance, similar biometric signals, for example, arterial blood pressures may be measured with a predetermined time difference therebetween. Referring to FIG. 6, a time-dependent first signal waveform S of the arterial blood pressure of the first light sensor 311 and a time-dependent second signal waveform P of the arterial blood pressure of the second light sensor 312 are illustrated. It may be seen that the first signal waveform S and the second signal waveform P are measured in similar forms and the phase of the first signal waveform S precedes the phase of the second signal waveform P. From the phase difference between the signal waveforms, it may be determined that a bloodstream flows from the first light sensor 311 to the second light sensor 312. Thus, when the phase of the first signal waveform S precedes the phase of the second signal waveform P in the wrist-type body component measuring apparatus 100 illustrated in FIG. 5, it may be determined that the wrist-type body component measuring apparatus 100 is worn on the left wrist. When the phase of the second signal waveform P precedes the phase of the first signal waveform S, it may be determined that the wrist-type body component measuring apparatus 100 is worn on the right wrist.

Figure 7:
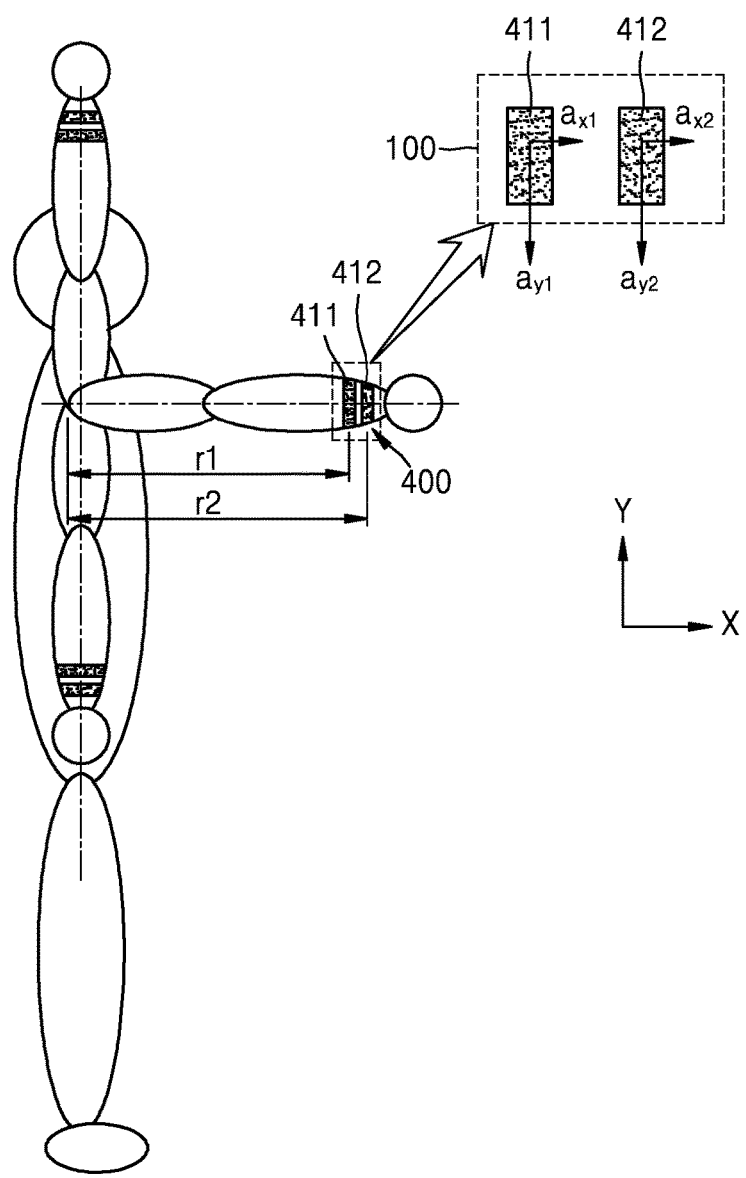
FIG. 7 is a diagram exemplarily illustrating an end portion of an arm when an object rotates the arm.

FIG. 7 is a diagram exemplarily illustrating an acceleration change of an end portion of an arm when the object rotates the arm.

The object may rotate the arm with the wrist-type body component measuring apparatus 100 worn thereon. In this case, an acceleration measuring apparatus including a plurality of acceleration sensors may be used to determine on which wrist, right or left, the wrist-type body component measuring apparatus 100 is worn.

Referring to FIG. 7, an acceleration measuring apparatus 400 includes a plurality of acceleration sensors 411 and 412 configured to sense an acceleration component generated when the object rotates the arm, and a processor configured to process signals sensed from the acceleration sensors 411 and 412. The acceleration sensors 411 and 412 may measure acceleration components of one or more of an X axis and a Y axis. When the object rotates the arm at an angular speed ω, an X-axis acceleration component $a_x$ and a Y-axis acceleration component $a_y$ may be expressed as below.

$$a_x = r\omega^2, a_y = r\dot{\omega}$$

The first acceleration sensor 411 and the second acceleration sensor 412 may be disposed on the inside surface STb of the strap ST or the main body MB of the wrist-type body component measuring apparatus 100 with a predetermined distance therebetween, and may be arranged in a direction perpendicular to the lengthwise direction of the strap ST. Since the first acceleration sensor 411 and the second acceleration sensor 412 are spaced apart from each other by a predetermined distance, their rotation radiuses on the elbow or shoulder of the object are different from each other. Thus, an X-axis acceleration component $a_{x1}$ and a Y-axis acceleration component $a_{y1}$ of the first acceleration sensor 411 having a first rotation radius $r_1$ and an X-axis acceleration component $a_{x2}$ and a Y-axis acceleration component $a_{y2}$ of the second acceleration sensor 412 having a second rotation radius $r_2$ may be expressed as below.

$$a_{x1} = r_1\omega^2, a_{y1} = r_1\dot{\omega}$$

$$a_{x2} = r_2\omega_2, a_{y2} = r_2\dot{\omega}$$

In this case, since the first acceleration sensor 411 and the second acceleration sensor 412 are disposed on the same rotation track, an angular speed ω of the first acceleration sensor 411 and an angular acceleration $\dot{\omega}$ of the second acceleration sensor 412 are equal to each other.

In the wrist-type body component measuring apparatus 100 illustrated in FIG. 7, when the X-axis acceleration component $a_{x2}$ or the Y-axis acceleration component $a_{y2}$ of the second acceleration sensor 412 is greater than the X-axis acceleration component $a_{x1}$ or the Y-axis acceleration component $a_{y1}$ of the first acceleration sensor 411, the second rotation radius $r_2$ of the second acceleration sensor 412 is greater than the first rotation radius $r_1$ of the first acceleration sensor 411. Thus, it may be determined that the wrist-type body component measuring apparatus 100 is worn on the right wrist.

When the X-axis acceleration component $a_{x2}$ or the Y-axis acceleration component $a_{y2}$ of the second acceleration sensor 412 is smaller than the X-axis acceleration component $a_{x1}$ or the Y-axis acceleration component $a_{y1}$ of the first acceleration sensor 411, the second rotation radius $r_2$ of the second acceleration sensor 412 is smaller than the first rotation radius $r_1$ of the first acceleration sensor 411. Thus, it may be determined that the wrist-type body component measuring apparatus 100 is worn on the left wrist.

As described above, the input unit 171 of the user interface 170 or the sensor may be used to determine on which wrist, right or left, the wrist-type body component measuring apparatus 100 is worn. The relative positions of the plurality of electrodes may be changed according to on which wrist, right or left, the wrist-type body component measuring apparatus 100 is worn. Therefore, in order to measure a body impedance having a small change value depending on the measurement positions, the relative positions of the plurality of electrodes should also be changed according to on which wrist, right or left, the wrist-type body component measuring apparatus 100 is worn.

Figure 8:
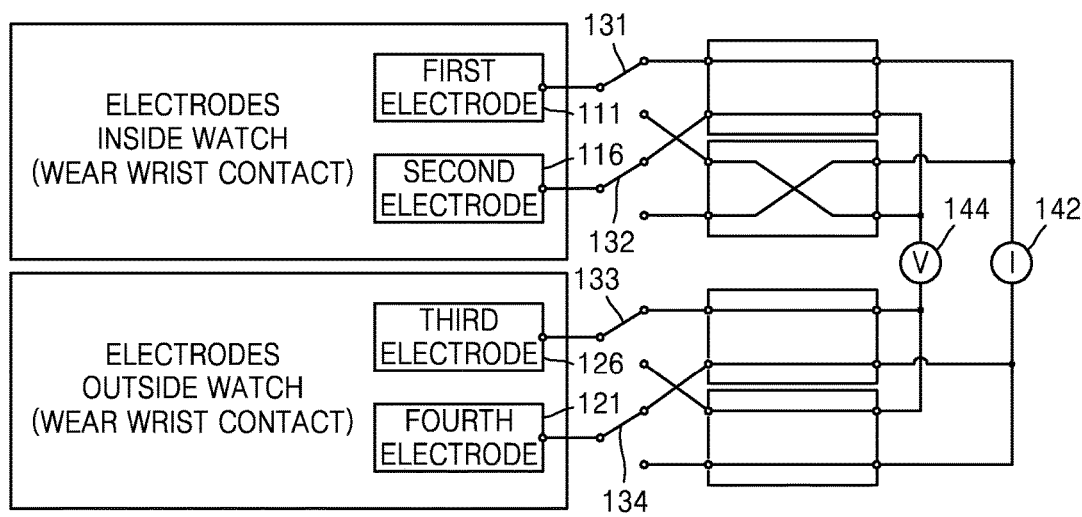
FIG. 8 illustrates a plurality of electrode units and a circuit diagram connected thereto according to an exemplary embodiment.
Figure 9A:
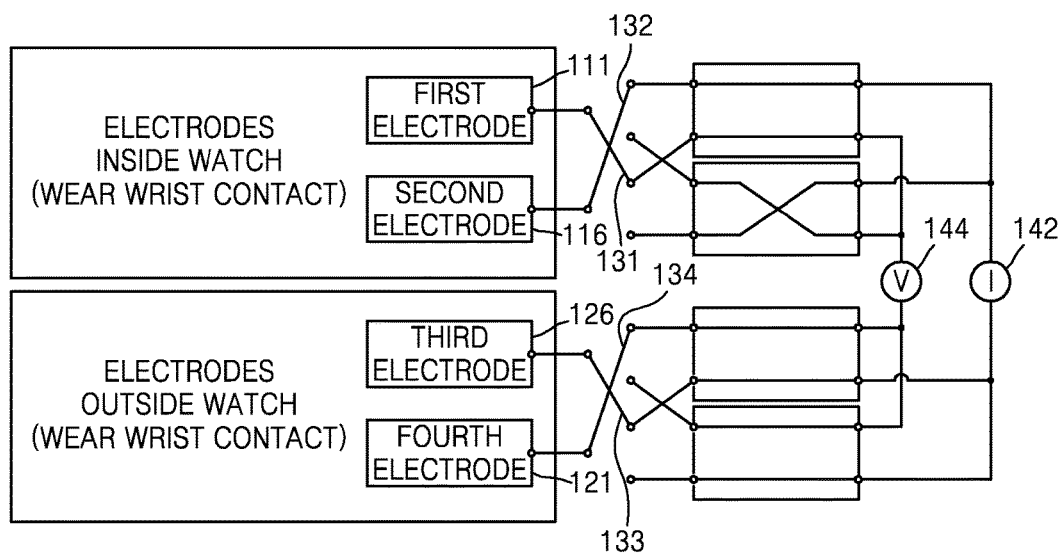
FIGS. 9A and 9B illustrate a plurality of electrode units, which have changed in relative positions, and a circuit diagram connected thereto according to an exemplary embodiment.
Figure 9B:
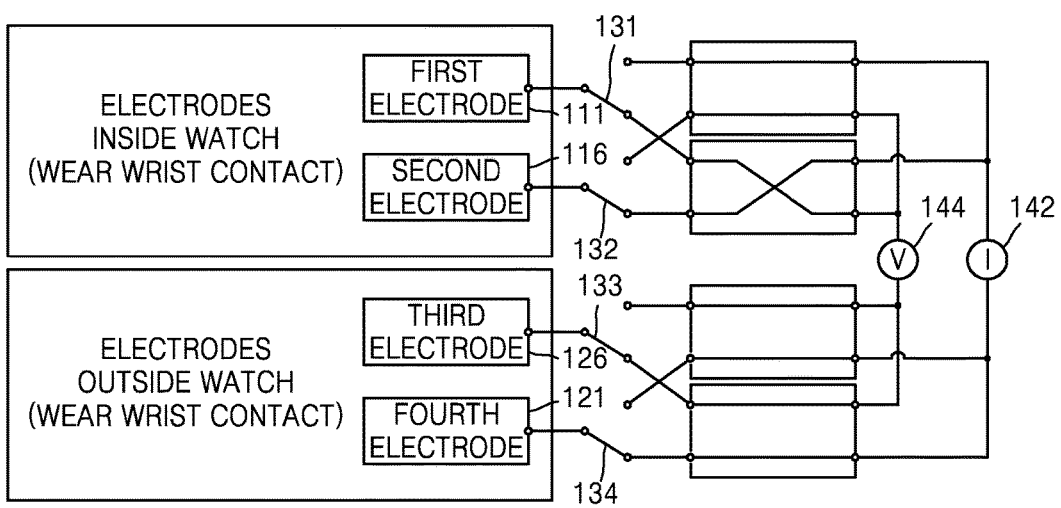

FIG. 8 illustrates a plurality of electrode units and a circuit diagram connected thereto according to an exemplary embodiment. FIGS. 9A and 9B illustrate a plurality of electrode units, which have changed in relative positions, and a circuit diagram connected thereto according to an exemplary embodiment.

Referring to FIGS. 1A, 1B, and 8, a first electrode 111 and a second electrode 116 are disposed on the inside surface STb of the strap ST, and a third electrode 126 and a fourth electrode 121 are disposed on the outside surface STa of the strap ST. In this case, the first electrode 111 and the fourth electrode 121 are a pair of current electrodes that are disposed on the hand side of the object and connected to both terminals of the current provider 142. The second electrode 116 and the third electrode 126 are a pair of voltage electrodes that are disposed on the body side of the object and connected to both terminals of the voltage detector 144. The first, second, third, and fourth electrodes 111, 116, 126, and 121 are connected to fixed terminals of a circuit unit by first, second, third, and fourth switches 131, 132, 133, and 134.

The object may change the side type of the wrist on which the wrist-type body component measuring apparatus 100 is worn. For example, when the wrist on which the wrist-type body component measuring apparatus 100 is worn changes from the left wrist to the right wrist, the first electrode 111 and the fourth electrode 121 are disposed on the body side of the object and the second electrode 116 and the third electrode 126 are disposed on the hand side of the object. In this case, when the first electrode 111 and the fourth electrode 121 are a pair of current electrodes and the second electrode 116 and the third electrode 126 are a pair of voltage electrodes, the pair of current electrodes are disposed on the body side of the object and the pair of voltage electrodes are disposed on the hand side of the object, so that a body impedance having a relatively large variation may be measured. In this case, when the first electrode 111 and the fourth electrode 121 are converted into the pair of voltage electrodes and the second electrode 116 and the third electrode 126 are converted into the pair of current electrodes, a body impedance having a relatively small variation may be measured.

As an example, switches may be used as an electrode converter that converts the disposition of the pair of current electrodes and the pair of the voltage electrodes. For example, referring to FIG. 9A according to an exemplary embodiment, the connections of the first switch 131 and the second switch 132 are changed such that the first switch 131 connected to the first electrode 111 is connected to one terminal of the voltage detector 144 and the second switch 132 connected to the second electrode 116 is connected to one terminal of the current provider 142. Also, the connections of the third switch 133 and the fourth switch 134 are changed such that the third switch 133 connected to the third electrode 126 is connected to one terminal of the current provider 142 and the fourth switch 134 connected to the fourth electrode 121 is connected to one terminal of the voltage detector 144. Accordingly, the second electrode 116 and the third electrode 126 may be connected to both terminals of the current provider 142, and the first electrode 111 and the fourth electrode 121 may be connected to both terminals of the voltage detector 144. Thus, even when the wrist on which the wrist-type body component measuring apparatus 100 is worn changes from the left wrist to the right wrist, the pair of current electrodes (i.e., the second electrode 116 and the third electrode 126) connected to both terminals of the current provider 142 may be disposed on the hand side and the pair of voltage electrodes (i.e., the first electrode 111 and the fourth electrode 121) connected to both terminals of the voltage detector 144 may be disposed on the body side.

As another example, an additional circuit configuration may be used to convert the disposition of the pair of current electrodes and the pair of the voltage electrodes. For example, referring to FIG. 9B according to an exemplary embodiment, an additional circuit diagram is connected to both terminals of the voltage detector 144, and an additional circuit diagram is connected to both terminals of the current provider 142. The connections of the first switch 131 and the second switch 132 are changed such that the first switch 131 connected to the first electrode 111 is connected to one terminal of the voltage detector 144 of the additional circuit diagram and the second switch 132 connected to the second electrode 116 is connected to one terminal of the current provider 142 of the additional circuit diagram. Also, the connections of the third switch 133 and the fourth switch 134 are changed such that the third switch 133 connected to the third electrode 126 is connected to one terminal of the current provider 142 of the additional circuit diagram and the fourth switch 134 connected to the fourth electrode 121 is connected to one terminal of the voltage detector 144 of the additional circuit diagram. Accordingly, the second electrode 116 and the third electrode 126 may be connected to both terminals of the current provider 142, and the first electrode 111 and the fourth electrode 121 may be connected to both terminals of the voltage detector 144. Thus, even when the wrist on which the wrist-type body component measuring apparatus 100 is worn changes from the left wrist to the right wrist, the pair of current electrodes (i.e., the second electrode 116 and the third electrode 126) connected to both terminals of the current provider 142 may be disposed on the hand side and the pair of voltage electrodes (i.e., the first electrode 111 and the fourth electrode 121) connected to both terminals of the voltage detector 144 may be disposed on the body side. However, exemplary embodiments are not limited thereto, and an electrical configuration or a structural modification may also be used to change the disposition of the pair of voltage electrodes and the pair of the current electrodes according to on which wrist, right or left, the wrist-type body component measuring apparatus 100 is worn.

Figure 10:
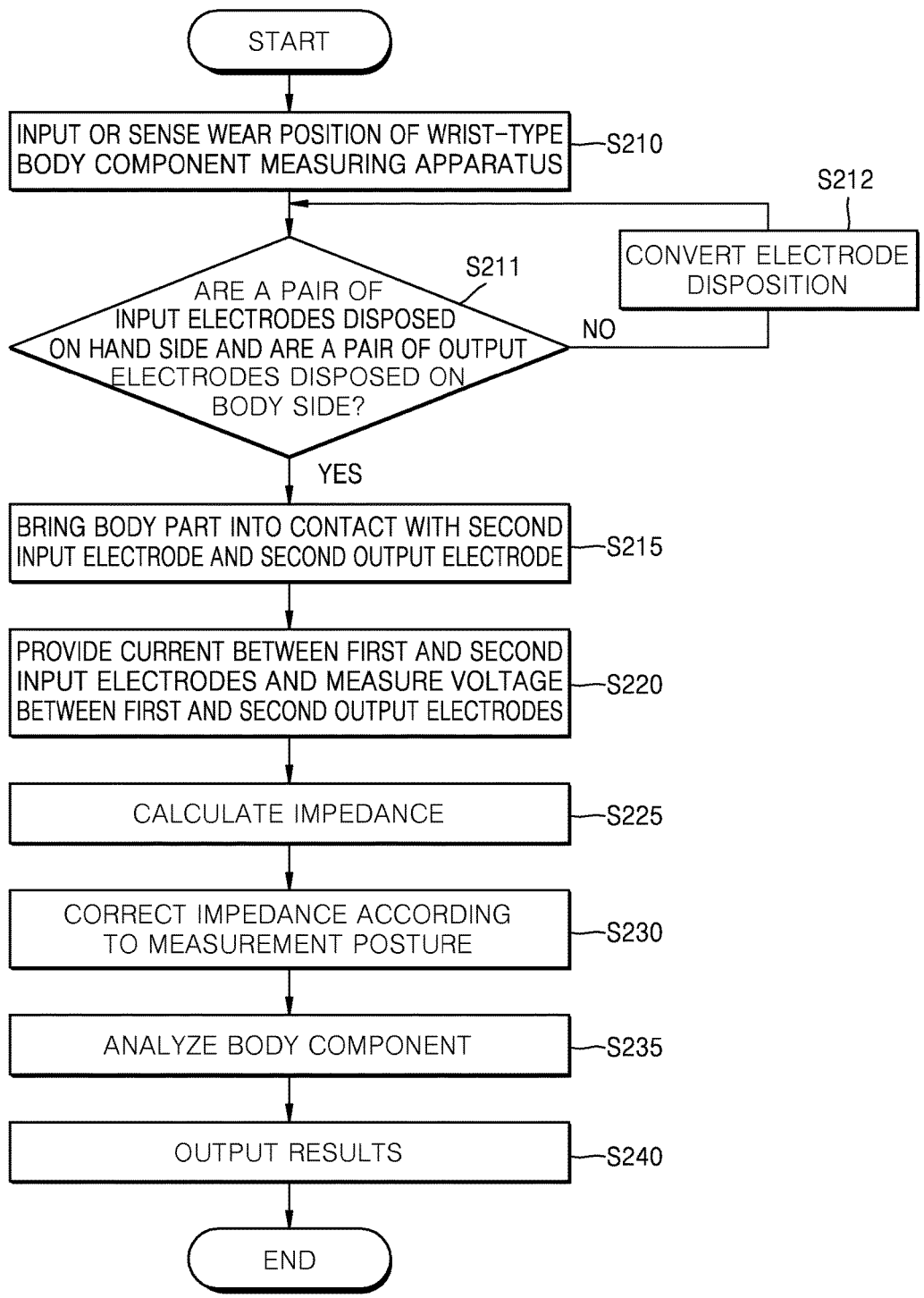
FIG. 10 is a flowchart schematically illustrating a body component measuring method according to an exemplary embodiment.

FIG. 10 is a flowchart schematically illustrating a body component measuring method according to an exemplary embodiment.

Information about a wrist wearing the wrist-type body component measuring apparatus 100. The information may indicate which wrist, left or right, a user is wearing the apparatus 100. The information may be input by the user or sensed by the sensor (operation S210).

According to on which wrist, right or left, the wrist-type body component measuring apparatus 100 is worn, it is determined whether a pair of input electrodes are disposed on the hand side and a pair of output electrodes are disposed on the body side (operation S211). The hand side and the body side mean positions relative to each other. Specifically, the hand side may refer to a position which is farther from the center of the body than the body side.

When the pair of input electrodes are disposed on the body side and the pair of output electrodes are disposed on the hand side, the electrode disposition is converted by switches (operation S212).

When the pair of input electrodes are disposed on the hand side and the pair of output electrodes are disposed on the body side, a relevant body part is brought into contact with the second input electrode and the second output electrode (operation S215).

The measuring unit provides a current between the first and second input electrodes and measures a voltage between the first and second output electrodes (operation S220).

An impedance is calculated from the provided current and the measured voltage (operation S225). The calculated impedance may be $Z_a+Z_{body}$ or $Z_{body}$ as illustrated above. $Z_a$ is an impedance of a contacted end body part a.

A body component is analyzed from the calculated body impedance (operation S235).

The body component analysis results are output in the form of an image or a text (operation S240).

For impedance correction (operation S230), the impedance of the end body part which is used for measurement may be pre-measured and stored.

As described above, according to the one or more of the above exemplary embodiments, the wrist-type body component measuring apparatus may measure the body component of the object by measuring the impedance of the object with relatively high accuracy.

Also, since the electrode disposition may be converted by sensing the mode of wearing the wrist-type body component measuring apparatus on the object, the wear freedom degree of the wrist-type body component measuring apparatus is high and thus the convenience of the object may be increased.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present disclosure can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A wrist-type body component measuring apparatus comprising:

a band configured to be worn on a user;
a first input electrode and a first output electrode which are disposed on an inside surface of the band and configured to contact a wrist of the user;
a second input electrode and a second output electrode which are disposed on an outside surface of the band;
a measuring unit configured to apply a current to the first and second input electrodes and detect a voltage from the first and second output electrodes to measure a body impedance of the user;
an input interface configured to receive, from the user, information about whether the band is worn on a left wrist or a right wrist of the user; and
an electrode converter configured to convert a disposition of the first and second input electrodes and the first and second output electrodes according to the information about whether the band is worn on the left wrist or the right wrist.

2. The wrist-type body component measuring apparatus of claim 1, wherein the measuring unit comprises:
a current provider configured to apply the current to the first and second input electrodes;
a voltage detector configured to detect the voltage from the first and second output electrodes; and
an impedance calculator configured to calculate the body impedance from the current and the voltage.

3. The wrist-type body component measuring apparatus of claim 2, wherein the electrode converter comprises a plurality of switches configured to change a first connection between each of the first and second output electrodes and the voltage detector and a second connection between each of the first and second input electrodes and the current provider to a third connection between each of the first and second output electrodes and the current provider and a fourth connection between each of the first and second input electrodes and the voltage detector.

4. The wrist-type body component measuring apparatus of claim 1, wherein an arrangement direction of the first input electrode and the first output electrode and an arrangement direction of the second input electrode and the second output electrode are different from a lengthwise direction of the band.

5. The wrist-type body component measuring apparatus of claim 4, wherein the arrangement direction of the first input electrode and the first output electrode and the arrangement direction of the second input electrode and the second output electrode are perpendicular to the lengthwise direction of the band.

6. The wrist-type body component measuring apparatus of claim 5, wherein the electrode disposition is converted such that the first input electrode and the second input electrode are disposed on a hand side of the wrist and the first output electrode and the second output electrode are disposed on a body side of the wrist based on the information about whether the band is worn on the left wrist or on the right wrist.

7. The wrist-type body component measuring apparatus of claim 1, wherein a body component of the user is analyzed from the body impedance measured by the measuring unit, and
the body component comprises at least one of body fat, body water, skeletal muscle mass, protein, mineral, visceral fat, body cell mass, bone mineral content, muscle strength, and edema.

8. The wrist-type body component measuring apparatus of claim 1, further comprising a memory configured to store an impedance of an end body part of the user that is to be in contact with the second input electrode and the second output electrode, for body impedance measurement.

9. A wrist-type body component measuring apparatus comprising:
a band configured to be worn on a user;
a first input electrode and a first output electrode which are disposed on an inside surface of the band and configured to contact a wrist of the user;
a second input electrode and a second output electrode which are disposed on an outside surface of the band;
a measuring unit configured to apply a current to the first and second input electrodes and detect a voltage from the first and second output electrodes to measure a body impedance of the user;
a plurality of acceleration sensors arranged in a direction perpendicular to a lengthwise direction of the apparatus with a predetermined distance therebetween, and configured to sense whether the band is worn on a left wrist or on a right wrist by using a signal received according to a movement of the user; and
an electrode converter configured to convert a disposition of the first and second input electrodes and the first and second output electrodes according to whether the band is worn on the left wrist or the right wrist of the user.

10. A wrist-type body component measuring apparatus comprising:
a band configured to be worn on a user;
a first input electrode and a first output electrode which are disposed on an inside surface of the band and configured to contact a wrist of the user;
a second input electrode and a second output electrode which are disposed on an outside surface of the band;
a measuring unit configured to apply a current to the first and second input electrodes and detect a voltage from the first and second output electrodes to measure a variation of a body impedance of the user when the second input electrode is sequentially touched by different fingers of the user;
a memory configured to store a reference body impedance variation; and
an electrode converter configured to compare the measured variation of the body impedance of the user to the reference body impedance variation that is stored in the memory and convert a disposition of the first and second input electrodes and the first and second output electrodes according to a comparison between the measured variation of the body impedance of the user and the reference body impedance variation.

11. The wrist-type body component measuring apparatus of claim 10, wherein the measuring unit comprises:
a current provider configured to apply the current to the first and second input electrodes;
a voltage detector configured to detect the voltage from the first and second output electrodes; and
an impedance calculator configured to calculate an impedance of the user from the current and the voltage.

12. The wrist-type body component measuring apparatus of claim 11, wherein the electrode converter comprises a plurality of switches configured to change a first connection between each of the first and second output electrodes and the voltage detector and a second connection between each of the first and second input electrodes and the current provider to a third connection between each of the first and second output electrodes and the current provider and a fourth connection between each of the first and second input electrodes and the voltage detector.

13. The wrist-type body component measuring apparatus of claim 11, wherein a body component of the user is analyzed from the impedance of the user, and
the body component comprises at least one of body fat, body water, muscle strength, and edema.

14. The wrist-type body component measuring apparatus of claim 10, wherein an arrangement direction of the first input electrode and the first output electrode and an arrangement direction of the second input electrode and the second output electrode are different from a lengthwise direction of the apparatus.

15. The wrist-type body component measuring apparatus of claim 14, wherein the arrangement direction of the first input electrode and the first output electrode and the arrangement direction of the second input electrode and the second output electrode are perpendicular to the lengthwise direction of the apparatus.

16. The wrist-type body component measuring apparatus of claim 15, wherein the electrode disposition is converted such that the first input electrode and the second input electrode are disposed on a hand side of the wrist and the first output electrode and the second output electrode are disposed on a body side of the wrist.

* * * * *